United States Patent
Sautter et al.

(10) Patent No.: US 7,187,440 B2
(45) Date of Patent: Mar. 6, 2007

(54) HOLOGRAPHIC SENSOR, ESPECIALLY FOR RECOGNITION OF MOISTURE ON A GLASS PANE OF A MOTOR VEHICLE

(75) Inventors: Helmut Sautter, Ditzingen (DE); Stefan Stampfer, Buehl (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/432,754

(22) PCT Filed: Jun. 25, 2002

(86) PCT No.: PCT/DE02/02319

§ 371 (c)(1),
(2), (4) Date: Nov. 12, 2003

(87) PCT Pub. No.: WO03/026937

PCT Pub. Date: Apr. 3, 2003

(65) Prior Publication Data

US 2004/0075828 A1    Apr. 22, 2004

(30) Foreign Application Priority Data

Sep. 26, 2001   (DE) ................................ 101 47 447

(51) Int. Cl.
*G01N 21/00*   (2006.01)
*G01N 21/55*   (2006.01)

(52) U.S. Cl. .................................... 356/239.8; 356/445

(58) Field of Classification Search .. 356/237.1–237.3, 356/239.1–239.8, 445–448; 250/573, 574, 250/227.25, 216, 221, 222.2, 341.8
See application file for complete search history.

(56) References Cited

U.S. PATENT DOCUMENTS

| | | | | |
|---|---|---|---|---|
| 5,661,303 A | * | 8/1997 | Teder | 250/341.8 |
| 5,998,782 A | * | 12/1999 | Koyama et al. | 250/227.25 |
| 6,147,753 A | * | 11/2000 | Koyama et al. | 356/237.3 |
| 6,239,444 B1 | * | 5/2001 | Tanaka et al. | 250/573 |
| 6,285,037 B1 | * | 9/2001 | Koyama et al. | 250/574 |
| 2002/0040964 A1 | * | 4/2002 | Dausmann et al. | 250/227.25 |

FOREIGN PATENT DOCUMENTS

| | | | |
|---|---|---|---|
| DE | 197 01 258 | | 7/1997 |
| DE | 199 33 640 | | 2/2001 |
| DE | 100 49 401 | A1 * | 4/2002 |
| EP | 0 736 426 | | 10/1996 |
| EP | 0 999 104 | | 5/2000 |
| EP | 1 195 598 | | 4/2002 |

* cited by examiner

Primary Examiner—Michael P. Stafira
(74) Attorney, Agent, or Firm—Kenyon & Kenyon LLP

(57) ABSTRACT

A holographic sensor for recognizing moisture on a glass pane of a motor vehicle is provided, having a casing, a carrier layer, a diffractive element and an adhesive layer, the diffractive element being fixed, preferably glued, on the carrier layer. The diffractive element may be embodied as an embossed hologram.

4 Claims, 2 Drawing Sheets

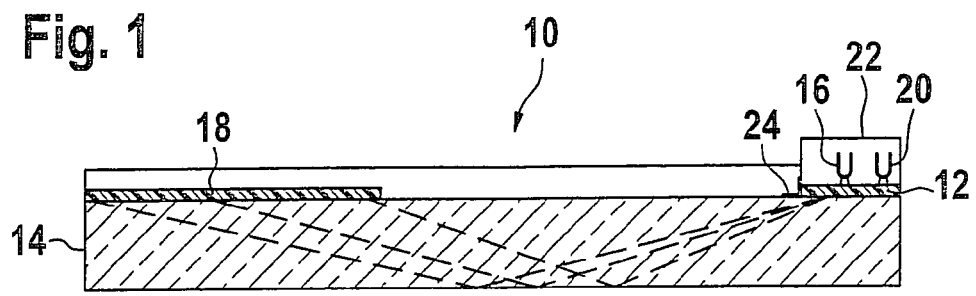
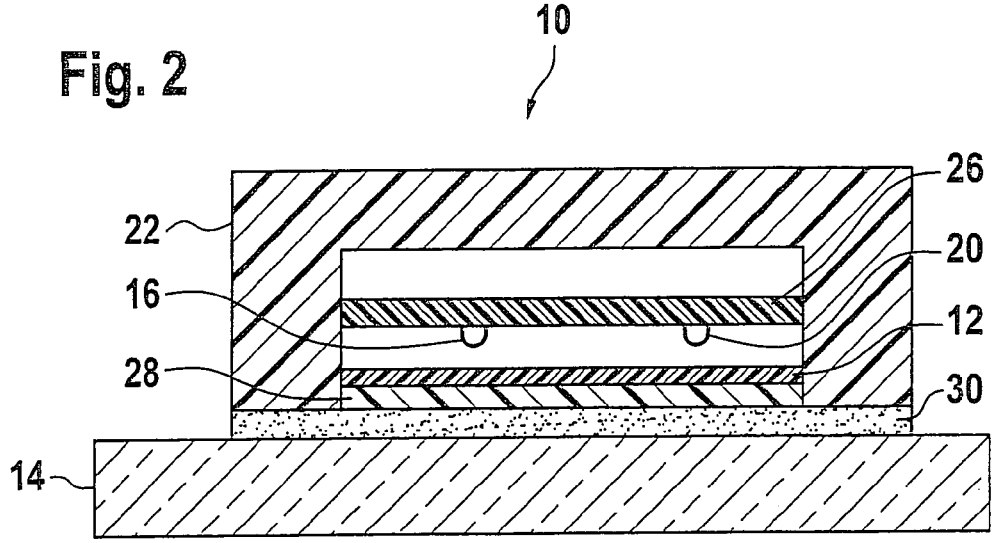
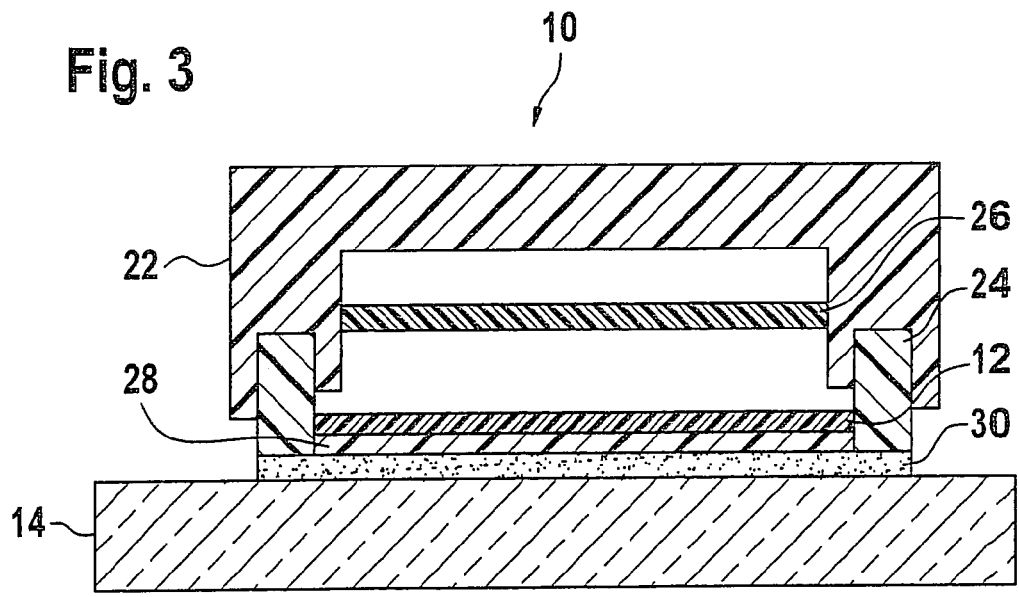

HOLOGRAPHIC SENSOR, ESPECIALLY FOR RECOGNITION OF MOISTURE ON A GLASS PANE OF A MOTOR VEHICLE

FIELD OF THE INVENTION

The present invention relates to a holographic sensor, in particular for recognizing moisture on a glass pane of a motor vehicle.

BACKGROUND INFORMATION

Sensors for recognizing moisture on a glass pane of a motor vehicle are discussed, for example from German Patent No. 199 33 640, but these sensors may be very large because of their complex, optical elements. Since the optical elements must be situated on the windshield of the motor vehicle in the region swept by the wiper, and are consequently in the visual range of the driver, the appropriate casing may distract the driver. This applies in particular because the relatively large casings require complex fixing elements, which are additionally provided on the glass pane. This may be complex and may be very costly in the series production.

A holographic sensor for recognizing drops of water on a glass pane is discussed in European Patent Application No. 999 104. In this reference, a hologram film is glued to or into the windshield.

SUMMARY OF THE INVENTION

A holographic sensor may have the advantage that the optical diffractive element is fixed on a carrier layer, which is glued to the windshield of the motor vehicle. A sensor assembly, including the diffractive element, may be manufactured in this manner as a compact structural element, which only needs to be glued to the windshield in the series production of motor vehicles. Through the compact design of the sensor, in particular by integrating all the components of the sensor within the casing, tolerances may be met more precisely, for example between the radiation transmitters and receivers and the optical structures of the diffractive element.

It may be advantageous if the carrier layer may be directly attached, preferably glued, to the glass pane of the motor vehicle. This may be easily overcome on the conveyor belt in the series production of motor vehicles, in particular since this requires only moderate tolerances.

Furthermore, it may be advantageous if at least one transmitter and/or at least one receiver are situated in the casing and the casing is connected to the carrier layer, thereby resulting in maximum dimensional stability of the individual components to one another. The sensor may be produced in such a manner and easily transported to the vehicle manufacturer without impeding the dimensional stability and the quality of the sensor.

It may be advantageous if the carrier layer is connected to at least one fixing element to which the casing is fixed. In this way, the sensor assembly may be glued to the glass pane of the motor vehicle, and for example in the case of repair, the casing may nevertheless be separated from the carrier layer having the diffractive element. Repairs to the optical or electronic components may consequently be made with less effort.

Furthermore, it may be advantageous if at least one transmitter and/or receiver are situated in the casing, able to emit or receive the radiation having at least one frequency f, and if the fixing element, at least in parts, is essentially transparent for the radiation of the at least one frequency f. The fixing element may then be attached with its entire surface to the glass pane and bears the carrier layer on which the diffractive element is provided. The casing is consequently connected to the glass pane of the motor vehicle with a very large adhesion surface area, resulting in a good bond of the sensor on the glass pane and preventing the sensor from falling down, even in extreme conditions.

Furthermore, it may be advantageous if the fixing element is designed as one piece with the carrier layer since a separate carrier layer may thereby be dispensed with and the cost of the sensor is reduced.

The holographic sensor may have the advantage that the diffractive element is designed as an embossed hologram, which is cheaper and easier to manufacture than optical holograms.

BRIEF DESCRIPTION OF THE DRAWINGS

FIG. 1 shows a schematic illustration of a holographic sensor.

FIG. 2 shows a schematic illustration of a section of a casing of a holographic sensor according to an exemplary embodiment of the present invention.

FIG. 3 shows an exemplary embodiment of a sensor according to the present invention having fixing elements.

DETAILED DESCRIPTION

Figure 4:
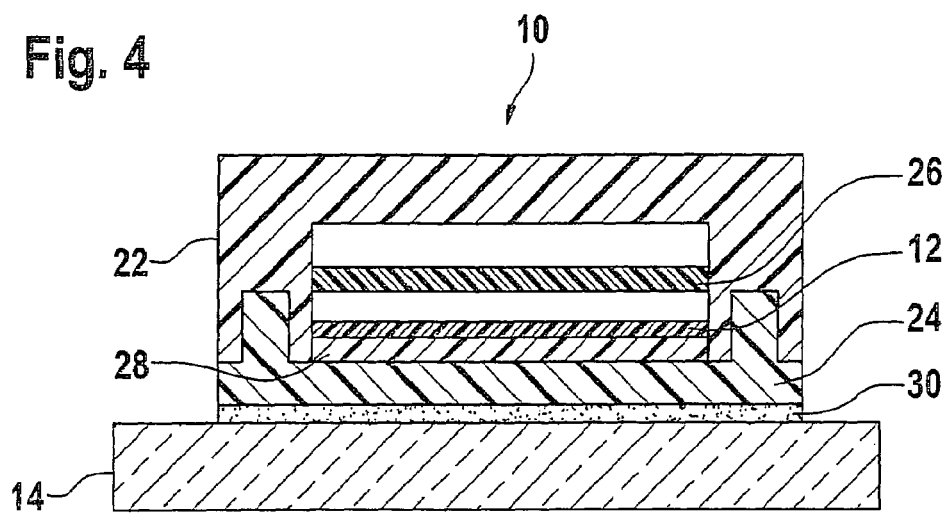
FIG. 4 shows another exemplary embodiment of the sensor according to the present invention.

FIG. 1 shows a holographic sensor in a schematic cross-sectional representation. Sensor 10 is essentially made up of a first diffractive element 12, which is glued to a glass pane 14. Diffractive element 12 is designed here as a holographic film. A transmitter 16, capable of emitting radiation having a frequency f, is positioned over diffractive element 12. In operation, transmitter 16 emits radiation having frequency f in the direction of diffractive element 12, which deflects this such that the radiation is completely reflected on the glass-air interface facing away from the sensor when glass pane 14 is dry.

After this complete reflection, the radiation reaches the glass-air interface of glass pane 14 facing the sensor, and is reflected there through another diffractive element 18, for example a retro reflector, and another complete reflection in the direction of diffractive element 12, which focuses the radiation toward a receiver 20.

Diffractive element 12 is designed in particular as a film or thin layer element, which using holographic structures deflects the radiation of transmitter 16 in one direction, for example through diffraction or refraction, and which is capable of coupling or decoupling the radiation in or from glass pane 14.

Transmitter 16, receiver 20, and diffractive element 12 are enclosed by a casing 22, which is fixed to glass pane 14 using fixing means 24.

In FIG. 2, a cross-section of a holographic sensor 10 according to the present invention is shown in schematic representation, but further diffractive element 18 was left out for reasons of clarity. A printed circuit board 26 is situated in casing 22, the printed circuit board bearing transmitter 16 and receiver 20. Casing 22 is essentially shell-shaped, whose interior space having printed circuit board 26 is sealed by a carrier layer 28. On the side facing the interior space of casing 22, carrier layer 28 bears diffractive element 12 so that the sensor casing, along with diffractive element 12, may be glued to glass pane 14 via an adhesive layer 30. This is may be an advantage in series production since diffractive element 12 need not be mounted separate from the remaining components of sensor 10.

In FIG. 3, a variation of the sensor according to the present invention from FIG. 2 is illustrated. Here, carrier layer 28 is rigidly connected to fixing means 24, to which casing 22 is fixed, in particular clipped, so that the electrical part of the casing containing printed circuit board 26 may be separated from the optical part containing diffractive element 12 and carrier layer 28, but may nevertheless be mounted as a whole on glass pane 14. Here, carrier layer 28 and fixing element 24 are rigidly connected to one another and are directly injected against one another in an injection molding process, for example.

FIG. 4 shows another variation of a sensor according to the present invention. Fixing element 24 extends in this case over the entire sensor region enclosed by casing 22. In addition, fixing element 24 is of course transparent for frequency f of transmitter 16 or of receiver 20 in the regions in which the radiation from diffractive element 12 must pass through carrier layer 28 and fixing element 24. Carrier layer 28 is provided directly on fixing element 24 on the inside of casing 22 and bears diffractive element 12. Adhesive layer 30 is provided on the side of fixing element 24, which is in contact with glass pane 14.

Figure 5:
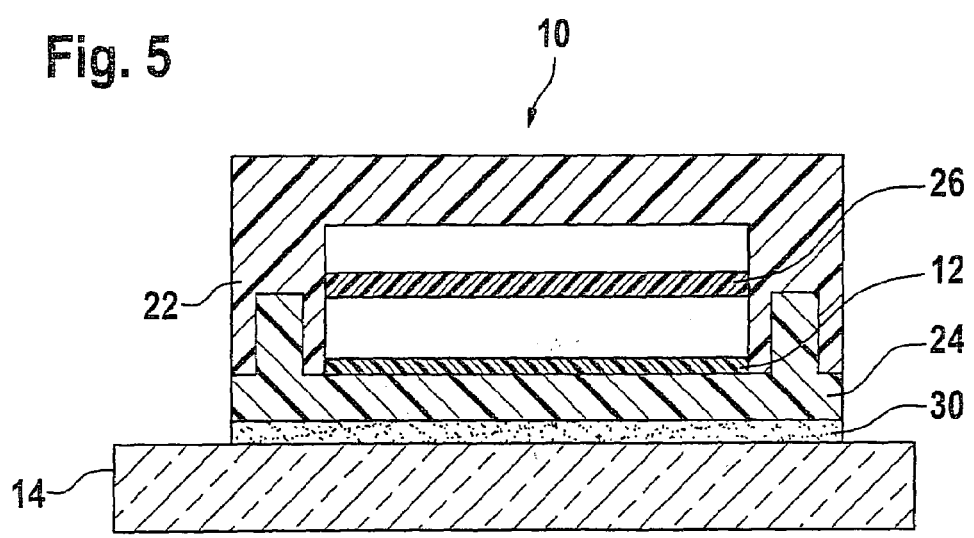
FIG. 5 shows yet another exemplary embodiment of a sensor according to the present invention.

In FIG. 5, a third variation of a holographic sensor 10 according to the present invention is shown. Here, diffractive element 12 is glued directly to fixing element 24 via an adhesive or also only through adhesion, so that carrier layer 28 and fixing element 24 are designed as one piece.

Conventional holograms manufactured by optical or mechanical means, i.e., stamped holograms, may be considered as diffractive element 12.

In particular, a plurality of diffractive elements 12, for example, one each for transmitter 16 and receiver 20, may also be provided.

The remaining components, such as fixing element 24 or casing 22, may be made from plastic, in particular as an injection-molded part. In principle, carrier layer 28 may of course also be pressed onto glass pane 14 and held on this via clamping or spring elements.

What is claimed is:

1. A holographic sensor, comprising:
   a casing;
   at least one diffractive element; and
   a carrier layer on which the at least one diffractive element is fixed, wherein the carrier layer is connected to at least one fixing element, wherein the casing is fixed to the fixing element, wherein the at least one fixing element is, at least in parts, substantially transparent for a radiation having at least one frequency, and wherein the carrier layer is configured to be attached directly to a glass pane.

2. The holographic sensor of claim 1, further comprising:
   at least one of a transmitter and a receiver arranged in the casing;
   wherein the casing is connected at least indirectly to the carrier layer.

3. The holographic sensor of claim 1, further comprising:
   at least one of a transmitter for transmitting and a receiver for receiving the radiation having the at least one frequency situated in the casing; wherein the at least one fixing element is configured to be attached to the glass pane.

4. The holographic sensor of claim 1, wherein the holographic sensor is adapted to recognize moisture on a glass pane of a motor vehicle.

* * * * *